United States Patent [19]

Johnson

[11] Patent Number: 4,807,611
[45] Date of Patent: Feb. 28, 1989

[54] PROPHYLACTIC DEVICE

[76] Inventor: Kenneth A. Johnson, Park Square Station, Box 15483, Stamford, Conn. 06901

[21] Appl. No.: 49,347

[22] Filed: May 13, 1987

[51] Int. Cl.4 .............................................. A61F 5/42
[52] U.S. Cl. .................................... 128/844; 604/349
[58] Field of Search ............... 604/389, 347, 349, 396; 128/132; D2/408, 10

[56] References Cited

U.S. PATENT DOCUMENTS

D. 288,485  2/1987  Denno .
3,486,507  12/1969  Bregenzer et al. ................. 2/408 X
3,536,066  10/1970  Ludwig ........................... 128/132 R Primary Examiner—Stephen C. Pellegrino
Attorney, Agent, or Firm—Kenyon & Kenyon

[57] ABSTRACT

A prophylactic device designed to isolate completely those portions of the body most susceptible to the introduction of infected bodily fluids of another into the bloodstream. The device includes a body portion fitting the wearer like a garment, extending from the vicinity of the navel downward to extend onto the thighs. A trap portion, either integral with or fixed to the body portion, covers the perineum of the wearer. The latter portion is formed of a highly expandable material and fitted loosely. The trap portion can respond to pressure from within or without to extend outwardly or inwardly to maintain an impermeable barrier between a penetrating member and the interior of a target orifice.

2 Claims, 2 Drawing Sheets

PROPHYLACTIC DEVICE

BACKGROUND OF THE INVENTION

This invention relates to the field of disease prevention, and more particularly to devices designed to prevent the spread of sexually transmitted diseases ("STD"'s).

The last decade has seen a remarkable rise both in the incidence of STD's and the impact of such diseases on the public consciousness. Penicillin and its progeny had relegated "traditional" STD's, such as gonorrhea, to a matter of little public concern by the end of the 1960's. That situation changed drastically, however, with the advent of herpes. A viral infection that proved resistant to all known forms of treatment, herpes presented a serious threat to persons who participated in frequent sexual activity with a number of partners. The public perception of the disease can be gauged from extensive media coverage, magazine articles and the like discussing the disease and its effect on sexual mores.

The impact of herpes, however, proved almost minuscule when the Acquired Immune Deficiency Syndrome (AIDS) epidemic surfaced in the 1980's. First identified only as a rare disease affecting homosexual men, the proportions of the problem exploded, with over 35,000 clinical AIDS cases currently, over 20,000 AIDS deaths, and with current estimates of up to 1.5 million infected Americans. Adding to the scope of the situation is the nature of the disease itself—simply put, no one has recovered from AIDS. The result has been an outpouring of concern, attention and research at all levels of society and government.

The nature of the disease contributes to the difficulty of preventing its spread. AIDS is caused by a virus, known as HIV, that attacks the human immune system— the body's mechanism for fighting infections and other diseases. By reducing (or, finally, eliminating) the body's ability to combat bacterial or viral invaders, AIDS does not kill directly, but results in a series of ever more debilitating infections or diseases that finally lead to the patient's death.

Transmission of the AIDS virus from an infected person appears to be most closely associated with a sharing of bodily fluids, most notably semen and blood. The transmission role of other body fluids, such as saliva, tears, vaginal lubricants, etc., cannot be clearly identified at this time, but it must be said that the AIDS virus has been cultured form all of these fluids. Research to date indicates that the most common modes of transmission are activities that allow either the semen or blood of an infected person to make contact with the bloodstream of another.

Thus, the activities primarily linked with AIDS transmission are many forms of sexual intercourse and the sharing of apparatus used in intravenous drug injection. The latter, for example, clearly exemplifies the bloodstream-to-bloodstream pathway for viral migration. In the sexual activities mentioned, the opportunity arises for transmission owing to the frequent presence of small lacerations or lesions in either the oral, vaginal or rectal mucosa, thereby allowing the virus to gain access to the bloodstream. Anal intercourse is an especially dangerous activity in this regard, inasmuch as the activity itself does produce breaks in the skin or mucal tissue. The disease is expected to mushroom among the heterosexual population in the not too distant future.

The discussion above focuses on transmission of virus at the precise site of the sexual activity, as does the bulk of public discussion. Brief consideration, however, demonstrates that such a narrow focus could underestimate the risks of infection, leading to inadequate preventive measures. Given the proclivity of the virus to exploit any break in the skin, the entire perineum should be considered a danger zone. This area is anatomically defined as the diamond-shaped portion of the body lying between the thighs and delimited at the posterior by the coccyx (tailbone), anteriorly by the symphysis pubis (the pubic bone) and laterally by the two ischial tuberosities. As is well known, this area is highly prone to rashes, pimples, and skin infections, all of which produce breaks in the skin surface. Given the likelihood of semen making contact with the perineal area in a variety of sexual circumstances, a high risk exists of infection through such skin breaks.

Overwhelmingly, suggestions aimed at limiting the spread of AIDS have concentrated on changing sexual behaviors seen as likely to transmit the virus (the so-called "safe sex" movement), and the use of condoms during sex. The former effort has achieved some success, but approaches aimed at fundamental changes in human nature historically have fallen short of widespread acceptance. Such measures had limited effect on the spread, successively, of gonorrhea, syphilis, and herpes, and it can be presumed that similar results will be observed for AIDS.

Failing a massive change in behavior patterns, many see the condom as the only real solution to the containment of AIDS. Several serious drawbacks to that solution, however, limit the success of this method of prevention. First, a particular condom may not fulfill its function, either because it does not remain in position, or it breaks during use, or it may remain in position but serve as a conduit for infectious biological products to travel onto the perineum. This problem is particularly acute in anogenital intercourse, due to the general lack of clearance between the orifice and the penis. The danger of relying upon the condom in such situations is exacerbated, of course, by the fact that this activity perhaps poses the greatest danger of infection.

More seriously, however, are the condom's inherent drawbacks. As mentioned above, the perineum offers a number of sites for viral entry to the bloodstream, yet the condom offers no protection whatsoever in this area. Moreover, spillage of semen from a condom is a common occurrence, and leakage is practically guaranteed, especialy when the wearer is supine. The condom is neither designed nor commonly used for the purpose of preventing contact between semen and the perineum of either or both partners, and thus it is not surprising that it does not serve that purpose. The risk presented by such contact, however, makes the condom a limited tool for preventing the spread of AIDS.

Additionally, the fact that the condom wearer or the partner must manually handle the condom after it has been used presents a high risk situation. Even if the used condom is handled carefully, avoiding spillage onto the perineal area (by no means an easy task), the occurrence of cuts, lacerations or lesions on the fingers or hands is common, and contact between such a skin break and semen from an infected person offers a ready path for entry of AIDS virus into the bloodstream.

The art has thus far failed to offer any solution having significantly more preventive utility than does the condom. In U.S. Pat. No., 3,759,254, Clark discloses a "Hygienic Appliances," consisting of a tubular condom-like member integral with a sack for covering the scrotum. Although this device does shroud the scrotum, it suffers from the inherent deficiencies of the condom, in that it allows for the free escape of semen and subsequent contact with skin breaks in the perineum.

A more comprehensive approach is seen in U.S. Pat. No. 3,536,066, entitled "Human Birth Control Appliances", issued to Ludwig. This device can essentially be described as a bikini-like garment incorporating in the front portion a reversible proboscis. The proboscis portion is formed with accordion-like bellows folds to allow for extension, and thus the area overlying the genitals initially is somewhat flat. From that position, the device can be worn by a man or woman, the proboscis extending respectively outward or inward to provide a physical barrier between the genitalia.

The limitations of this device inhere in its stated teaching that it is designed to prevent impregnation and additionally to prevent the transmission of venereal disease. It should be noted that the issuance of this patent, in 1970, antedates the problem of herpes by a number of years, and precedes the AIDS epidemic by over a decade. Thus, no thought is given to the risk of semen making contact with the perineum of either partner, a situation that the bikini design makes inevitable. Furthermore, the bellows fold design is particularly undesirable for use in anogenital intercourse, as the folds will make penetration more difficult than normal, and this sizing problem probably would altogether rule out the use of the device by both partners, which of course is the situation of maximum desirability. And not only would the device prove impossible or difficult to use in such situations, but it could aggravate the situation by causing more tissue damage than is normally associated with anogenital activity, thus increasing the chances of infection at that or a later time.

Thus it is seen that the art has failed to produce a device that affords a complete barrier between all areas susceptible to the introduction of AIDS, herpes virus, or other STD's into the bloodstream. It is that need that the present invention meets fully and conveniently.

SUMMARY OF THE INVENTION

It is an object of the present invention to provide a prophylactic device capable of being used by either males dor females to accomplish intravaginal, orogenital, oroanal or anogenital intercourse to provide a physical barrier between the perineal area of the wearer and the sexual partner.

It is a further object of the invention to provide a prophylactic device that permits the conduct of sexual activity without loss of tactile sensitivity, yet provides complete protection of the perineal area of both the wearer and the partner.

Yet another object of the invention is a prophylactic device that completely protects the perineum of the wearer from contact with either epidermal surfaces or bodily fluids of the partner during sexual activity.

Still another object of the invention is a prophylactic device that prevents spillage or leakage of seminal fluid during sexual activity.

These and other objects are achieved in the present invention in which there is provided a prophylactic device for use by a human wearer, comprising a body portion and a trap portion. The body portion is formed of flexible material and adapted to fit snugly on a human body, extending at least from the area adjacent the navel downward to a point below which the thighs intersect with the torso. This configuration insures that the entire perineum is isolated from contact with the sexual partner. The trap portion is fixed to the body portion to overlie the entire perineal area of a wearer, thus extending from slightly above the gential area in front to slightly above the anal area in the rear. This trap portion is formed of a smooth, extendible material for extending outwardly or inwardly to conform intimately with portions of the wearer in contact with the trap portion. This conformability allows the trap portion to be employed by either a male or female wearer.

The trap portion is preferably formed of a material extendible between a nonextended state and a fully extended state, such that the surface area of the trap portion in the fully extended state is at least four times greater than the surface area of the trap portion in the nonextended state. Such extendibility allows the trap portion to conform intimately with the body of the wearer, as discussed above, and thus insures the provision of tactile sensitivity for the wearer, as well as the ability to conduct anogenital intercourse without undue difficulty or tissue damage.

DETAILED DESCRIPTION OF A PREFERRED EMBODIMENT

Figure 1:
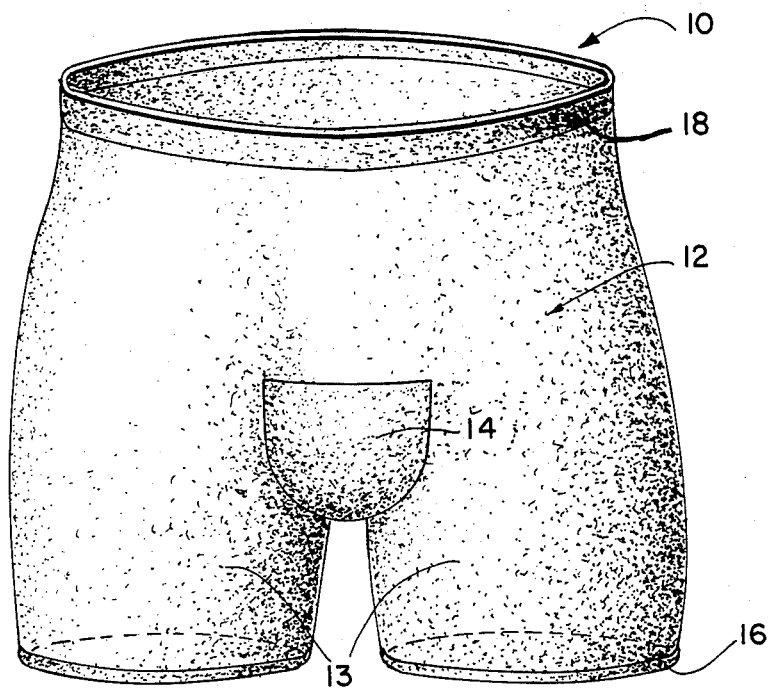
FIG. 1 is a pictorial representation of a prophylactic device according to the present invention, seen from the front.
Figure 2:
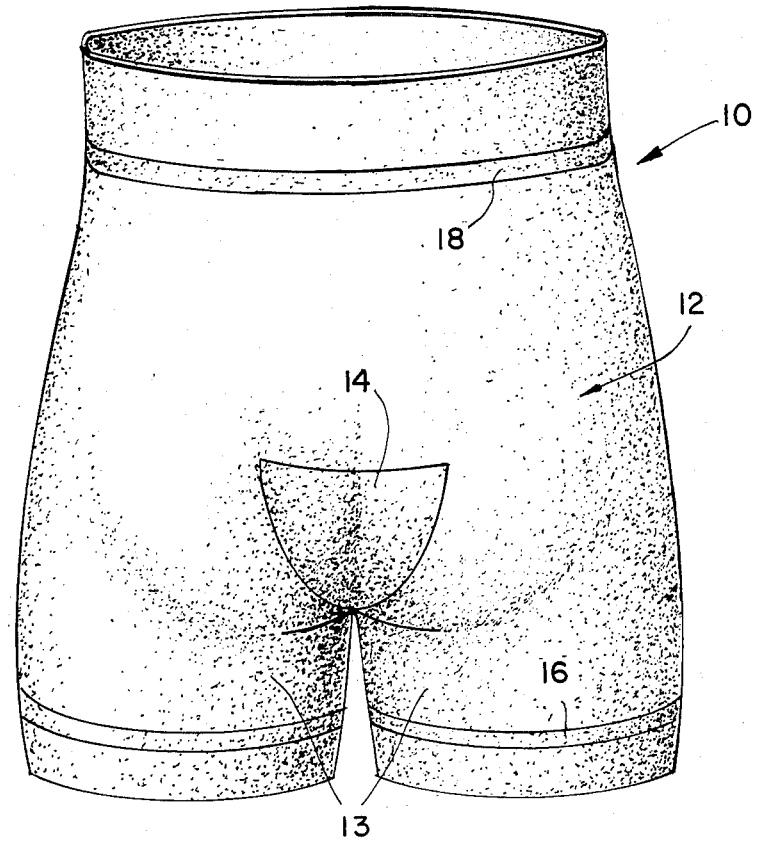
FIG. 2 is a pictorial representation of the prophylactic device of FIG. 1, seen from the rear.
Figure 3:
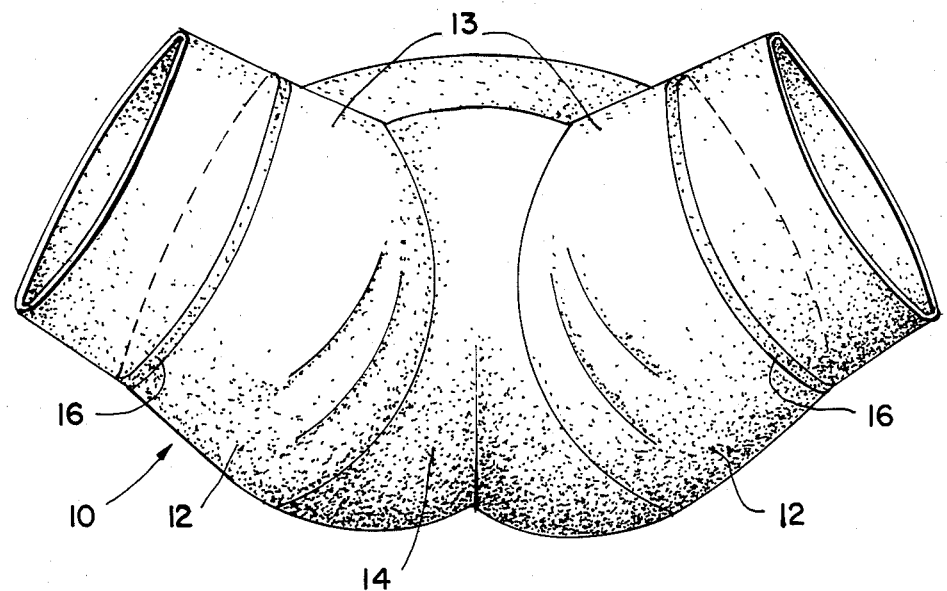
FIG. 3 is a pictorial representation of the prophylactic device of FIG. 1, seen from below.

A prophylactic device 10 according to the present invention is shown in FIGS. 1–3, in front (anterior), rear (posterior) and bottom (inferior) views. As used herein, the person designated the "wearer" is employing a prophylactic device according to the invention, and the "partner" may or may not be so equipped. As will be seen, the "wearer" and the "partner" may be any combination of male and female persons.

The body portion 12 of the device resembles a garment, covering the wearer from the vicinity of the wearer's navel downward and including thigh portions 13 that extend down onto the wearer's thighs for a distance at least sufficient to prevent the device from moving upward during use to expose the perineum to possible contact with a partner's bodily fluids. Preferably, the thigh portions are at least three inches in length, and may extend for six inches.

The body portion is adapted to fit a wearer snugly, and preferably such devices are provided in a range of sizes, as is known to those in the garment art. Openings at the waist and thighs are provided with security seals 18 and 16, respectively, for holding such openings closely to the wearer's body to prevent possible ingress or egress of fluids.

Materials for the body portion are discussed in more detail below, but important characteristics of such materials are flexibility, to allow the wearer to move into a number of positions readily and in comfort; elasticity, to mold the body portion closely to the wearer, both for increased security and to maintain the greatest degree of tactile sensitivity; and strength, to withstand vigorous use without tearing, while maintaining a liquid-tight barrier between the wearer and the partner.

The body portion is completely cut so that no portion of the body portion overlies the perineum, and the trap portion 14 is bonded to the body to cover that area. It is important that the trap portion be dimensioned completely to overlie the wearer's perineum, for an anterior position approximately covering the pubic bone to a posterior locaton approximately overlying the coccyx (tailbone). As best seen in FIG. 3, the sides of the trap portion should be approximately aligned with the line of intersection between the thighs and the torso. Bonding of the trap portion to the body portion may be accomplished in any suitable manner, as is known to those in the art.

The trap portion is dimensioned and fixed to the body so that it is very loose and flaccid, yet it does not have any structured folds or bellows. The surface of the trap is smooth, but is highly compressible and thus the surface can be easily wrinkled and warped. The specific material of the trap will be discussed in more detail below, but key characteristics are extreme extendibility, coupled with strength and impermeability. The material should be able to extend in surface area upon the application of pressure, between a nonextended state and an extended state. Preferably, the trap material in the fully extended state should have a surface area at least four times the surface area in the nonextended state, and more preferably the extension ratio should be five to one. Not only does such extendibility maintain tactile sensitivity, but more important it insures that the trap will not fail in tension during intercourse.

The preferred material for both the body and trap portions of the invention is latex rubber, of the type used in the production of conventional condoms. It has been found, however, that latex up to at least 6 mm in thickness provides the degree of expandability required for proper function of the invention. In one embodiment, the body portion and the trap portion are produced separately, using techniques known in the clothing and condom arts. For such a device, the body portion is preferably of greater thickness than the trap portion, with the body portion being about 6 mm thickness and the trap portion being about 2 mm thickness. Here, the two portions are joined by known operations, such as by sonic welding. Alternatively, the device can be formed as an integral unit, preferably by dip molding. In such a technique, the device would be of uniform thickness throughout, preferably at or below 6 mm.

In operation, the prophylactic device of the invention performs identically no matter what particular sexual activity is undertaken. The device is donned preferably before any activity is undertaken, to insure proper positioning and fit. Although many activities can be undertaken by couples in which only one partner employs the device, it must be emphasized that mutual orogenital or oroanal activity requires that both partners wear the device if both persons are to be protected. In any event, the full range of sexual activity is available if both persons wear the device, and thus it is recommended that both partners do so for maximum protection when required for mutual oroanal or orogenital activity.

Figure 4:
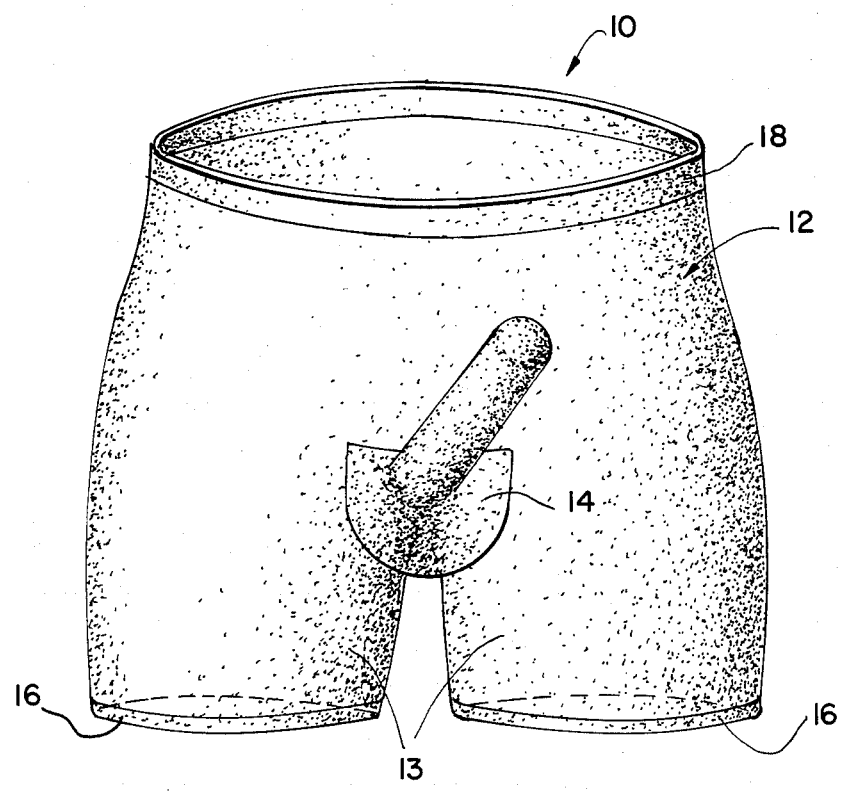
FIG. 4 is a pictoral representation of the prophylactic device of FIG. 1, showing the trap portion extended.

The trap portion responds to the application of pressure, whether exerted from within or without, by extending. FIG. 4 illustrates the device in an expanded state, assuming a male wearer. If the wearer assumes a passive role, the trap expands similarly but inwardly within the targen orifice. If desired, the trap portion can be lubricated as known in the art to assist penetration. During sexual activity, the expanded trap provides a complete and impermeable barrier between the penetrating member and the interior of the target orifice, regardless what particular activity is performed or what role is taken by the wearer.

It should be noted that the increase in surface area gained by covering the entire perineum with a single piece of trap material increases the total surface area of the trap portion, thus increasing the ability of a given part of the trap to extend yieldingly. This characteristic, in combination with the flaccid or loose fit of the trap portion eases the strain of penetration, benefiting the users and minimizing the tensile forces applied to a given small area of trap material. Furthermore, the fact that the trap material has a smooth surface and conforms closely around bodily parts enables the conduct of anogenital intercourse, unlike prior art devices.

The trap portion's flaccidity offers the further advantage of retaining expended bodily fluids, such as ejaculate, in a manner most likely to avoid contact with the partner. Especially if worn by a passive partner, the trap material will naturally fold around such fluids to prevent their migration within the device, a process assisted by the snug fit of the device.

After use, the device is removed by rolling it downward off of the wearer. This process allows trapped fluids to be contained within the device, preventing contact with a wearer's hands and possible transmission to a partner through that route.

Various modifications and alterations to the embodiment discussed above may be made within the spirit of the invention. For example, combinations of coloring, olfactory enhancements, taste enhancements, or graphic design elements could be introduced in the interest of heightening the sensory element associated with using the device. Alternatively, materials could be altered within the general descriptions given. These and other modifications may be made by those in the art without departing from the ambit of the invention, the scope of which is defined solely by the claims appended hereto.

I claim:

1. A prophylactic device for use by a human wearer, comprising:
   a body portion, formed of flexible material and adapted to fit snugly on a human body, extending at least from the area adjacent the navel downward to a point below which the thighs intersect the torso;
   a trap portion, integral with said body portion and overlying the perineal area of a wearer, formed of a smooth, nonfolded extendible material for extending outwardly or inwardly to conform intimately with portions of the wearer in contact with said trap portion, said material being extendible between a nonextended state and a fully extended state such that the surface area of said trap portion in such fully extended state is at least four times greater than the surface area of said trap portion in said nonextended state;
   said flexible material and said extendible material being impermeable to human bodily fluids.

2. In a prophylactic device for a human wearer, the device being formed as a garment and having an expandable area capable of expansion outwardly or inwardly, the improvement wherein the expandable area extends continuously to cover the entire perineum of the wearer;

is formed without structural folds;

is extensible between a nonextended state and a fully extended state such that the surface area of the expandable area in said fully extended state is at least four times greater than the surface area of the expandable area in said nonextended state; and is impermeable to human bodily fluids.

* * * * *